(12) United States Patent
Ascherman

(10) Patent No.: US 6,328,745 B1
(45) Date of Patent: Dec. 11, 2001

(54) PALATE EXPANDER

(75) Inventor: Jeffrey A. Ascherman, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/449,714

(22) Filed: Nov. 24, 1999

Related U.S. Application Data
(60) Provisional application No. 60/109,863, filed on Nov. 24, 1998.

(51) Int. Cl.[7] ........................................ A61F 5/00
(52) U.S. Cl. ................................... 606/86; 433/7
(58) Field of Search ................... 433/7, 16, 18; 606/86

(56) References Cited

U.S. PATENT DOCUMENTS

| | | | |
|---|---|---|---|
| 3,977,082 | * | 8/1976 | Siatkowski ................ 433/7 |
| 4,045,871 | * | 9/1977 | Nelson ..................... 433/7 |
| 4,347,054 | * | 8/1982 | Kraus et al. ............... 433/7 |
| 5,133,659 | * | 7/1992 | Shiliday ................... 433/3 |
| 5,281,133 | * | 1/1994 | Farzin-Nia ................ 433/7 |
| 5,439,377 | * | 8/1995 | Milanovich ............... 433/7 |
| 5,775,898 | * | 7/1998 | Schellino et al. ......... 433/7 |
| 5,904,479 | * | 5/1999 | Staples .................... 433/7 |
| 6,174,162 | * | 1/2001 | Pozzi ...................... 433/3 |

* cited by examiner

Primary Examiner—Gene Mancene
Assistant Examiner—Michael B. Priddy
(74) Attorney, Agent, or Firm—Cowan, Liebowitz & Latman, P.C.; William H. Dippert

(57) ABSTRACT

An expander for lengthening a patient's palate comprises two substantially rigid sections, each of which sections has one or more downwardly extending members capable of being affixed to a surface; and a threading system attached to each section, the threading system being capable of predictably adjusting the spacing between the rigid sections. The expander is useful for lengthening a patient's palate, for example, for the treatment of velopharyngeal incompetence.

3 Claims, 2 Drawing Sheets

PALATE EXPANDER

This application claims the benefit of provisional application No. 60/109,863, filed on Nov. 24, 1998.

FIELD OF THE INVENTION

This invention relates to a palate expander. More particularly, this invention relates to an apparatus and method for expanding a palate in a posterior direction.

BACKGROUND OF THE INVENTION

Velopharyngeal incompetence is a condition in which the palate cannot adequately seal off the oral cavity from the nasal cavity, resulting in abnormal speech. It is sometimes present in patients who have had a cleft palate repaired, but it can also be caused by other conditions such as congenital palatal insufficiency, a situation in which the palate is too short to reach the posterior pharyngeal wall. Many corrective procedures for velopharyngeal incompetence have been described, including palatoplasties, pharyngoplasties, and pharyngeal flaps. No single operation has been predictively effective.

One of the main focuses of this invention, but not the only focus, is on cleft palate patients. These patients have been treated with a procedure whereby two portions of a divided palate have been joined together. In many instances the resulting repaired palate is short or relatively immobile, resulting in velopharyngeal incompetence to the extent that the patients have speech problems (often hypernasal speech).

OBJECTS OF THE INVENTION

It is an object of this invention to provide a method and apparatus for treating velopharyngeal incompetence.

It is also an object of this invention to provide a method and apparatus for lengthening a palate in the posterior direction.

It is a further object of the invention to provide a method and apparatus for improving the speech of a patient with hypernasal speech such as may be observed after a cleft palate is repaired.

These and other objects of the invention will become more apparent from the discussion below.

SUMMARY OF THE INVENTION

According to the invention, a patient's velopharyngeal incompetence is treated by causing a palate to be lengthened in the posterior direction. This procedure is known as "distraction osteogenesis." The palate is divided in a transverse fashion, and then an extender having "foot pads" is affixed to the separated sections of the palate. The extender comprises two main sections that are moved relative to each other by mechanical means, each section having one or two foot pads that are attached to a section of the separated palate. The extender is adjusted regularly to cause the anterior and posterior palate sections to slowly move apart The space between the sections tends to fill in with bone according to natural processes of healing. The result is that after an appropriate period of time the patient has a palate that is longer and now extends more posteriorly than before, thus helping to correct velopharyngeal incompetence.

DETAILED DESCRIPTION OF THE INVENTION

Figure 1:
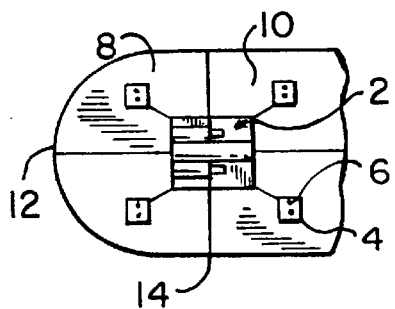
FIG. 1 is a top plan view of an expander according to the invention in position on two sections of a repaired cleft palate.
Figure 2:
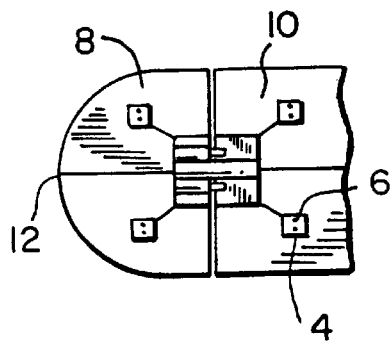
FIG. 2 is a top plan view of the embodiment of the invention shown in FIG. 1 where the sections of the cleft palate have been moved apart after the palate has been cut transversely.

The invention can perhaps be better appreciated from the embodiments of the invention set forth in FIGS. 1 to 6. In FIG. 1 an expander 2 has metal foot pads 4 that have been removably attached with metal screws 6 to palate sections 8 and 10, each of which comprise portions of a cleft palate that have been joined together previously at fusion point 12. Metal screws 6 extend through the metal pads 4 and attach the device to palate sections 8 and 10.

Typically there will be four pads 4, although the number of pads 4 could vary from 2 to 4. Each pad 4 will have at least one screw, preferably 2 or 3, and most probably 2 screws oriented transversely. The pad and screw configuration can vary dependent upon the palate to which the device is attached.

Prior to installation of expander 2, the palate was divided at line 14 to create sections 8 and 10. The severing can be done by known surgical means, such as using osteotomies (chisel-like instruments) to make the needed osteotomies, i.e., bone cuts. Additional osteotomies are made along each side of the posterior section 10 to separate this section from the teeth so that it can be advanced posteriorly independent of the teeth.

Expander 2 comprises threading system 16, which is capable of precise adjustment to carefully separate sections 18 and 20, and thus palate sections 8 and 10. For example, after expander 2 is installed, threading system 16 is adjusted to cause palate sections 8 and 10 to move apart approximately 0.5 to 1 mm per day for as many days as needed until the palate is sufficiently lengthened (or reaches the expander's maximum lengthening capacity of 10–20 mm). The screw 26 is turned by a narrow metal pin (not shown) that is temporarily inserted into a central hole in screw 26, and then rotated. After the screw 26 is turned, the pin is removed until it is next needed to turn screw 26.

Figure 3:
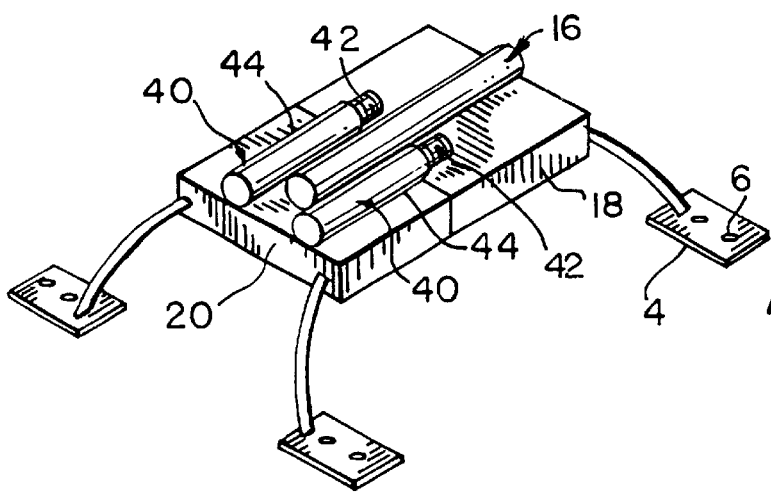
FIG. 3 is an oblique plan view of an expander useful according to the invention.

Expander 2 may have one or more threading systems 16. In FIG. 3, there is one centrally located threading system 16 and two guiding systems 40. Systems 40 can each comprise a rod 42 that is received in a cylinder 44.

Figure 4:
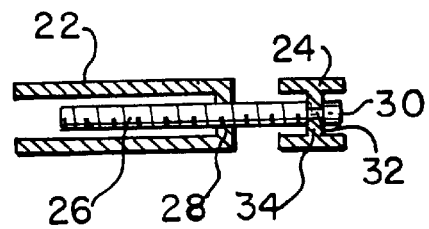
FIG. 4 is a partial cross-sectional view of a section of a threading system useful in the expander.

As shown in FIG. 4, a threading system 16 can comprise two aligned cylinders 22 and 24 where an internal screw 26 forces cylinders 22 and 24 apart. Screw 26 engages threading 28, while the distal end 30 of screw 26 has a recess 32 that rotates within annular ring 34 of cylinder 24.

Figure 5:
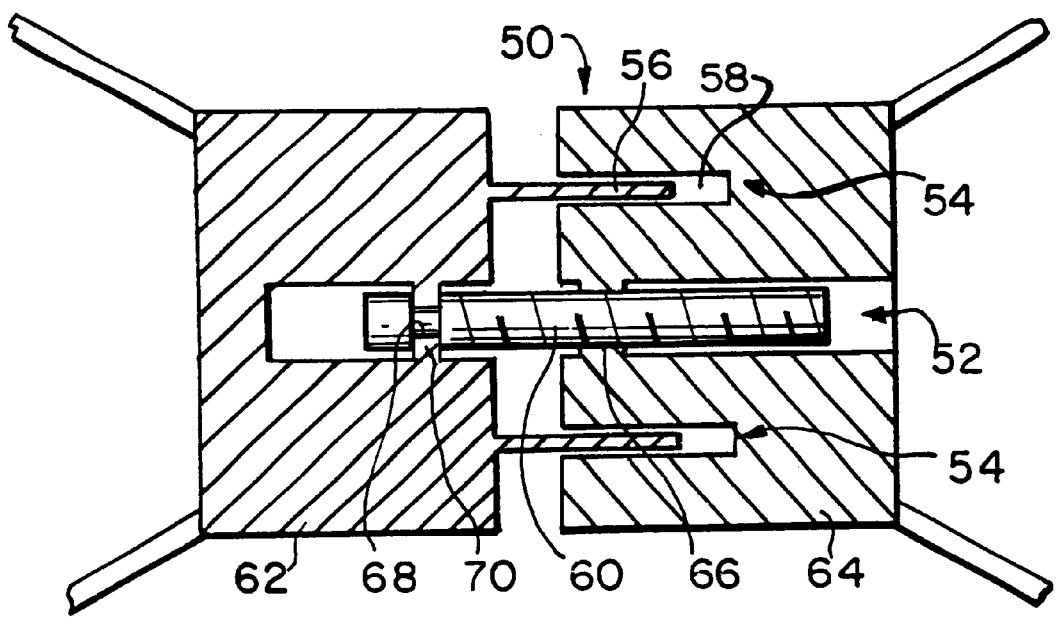
FIG. 5 and 6 are each a partial cross-sectional view of another expander useful according to the invention.

FIG. 5 represents a partial cross-sectional view of another embodiment of an expander 50, where the threading system 52 and guide systems 54 are internal. Each guide system 54 comprises a rod 56 which is received within a cylinder 58. Threading system 52 comprises an internal screw 60 that forces sections 62 and 64 apart. Screw 60 engages threading 66, while the distal end of screw 60 has a recess 68 that rotates within annual ring 70.

Figure 6:
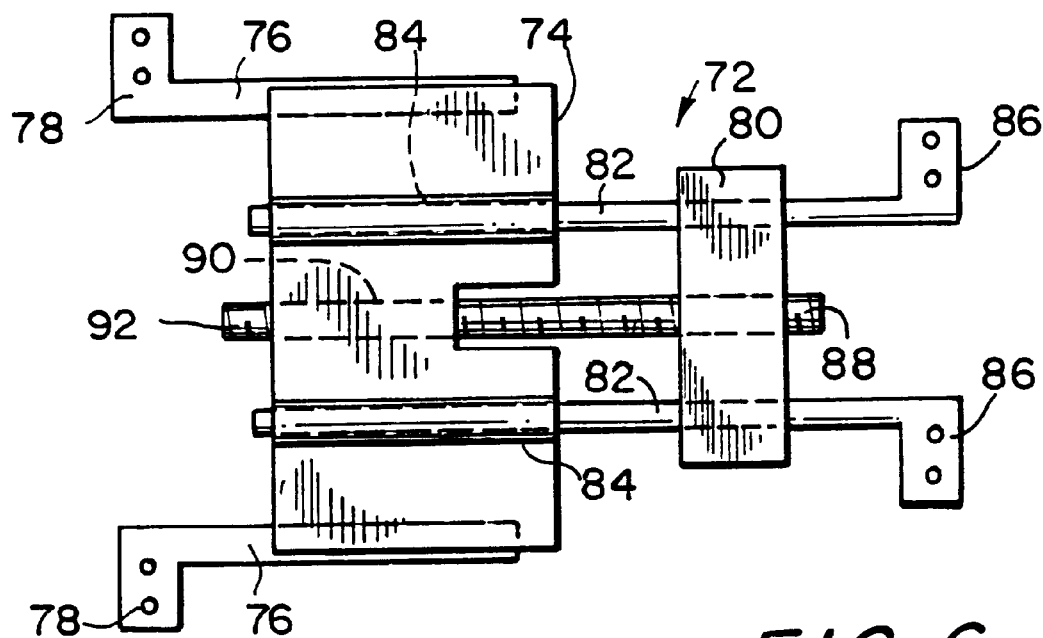

In FIG. 6 an expander 72 comprises a base unit 74 with legs 76 attached to foot pads 78. Screw unit 80 comprises guide pins 82 that extend to and are slidably received in channels or openings 84 in base unit 74. Screw unit 80 also comprises, or is attached to foot pads 86, which may comprise an extension of guide pins 82 or may have separate attaching members. Screw member 88, which is rotatably but attached to screw unit 80, extends into threaded opening 90 in base unit 74. When the proximal end 92 of screw member 88 is turned, the spacing between base unit 74 and screw unit 80, and thus between foot pads 78 and foot pads 86, is adjusted.

The expander and its components are made from suitable rigid, sterilizable, preferably metallic, materials. Useful materials include titanium, stainless steel, nitinol, and similar alloys. It is within the scope of the invention that rigid polymeric materials could be used as well.

Certain testing regarding the invention has been conducted The purpose of one study was to determine if a canine hard palate can be lengthened by distraction osteogenesis in a cleft palate model. The testing was conducted as follows:

Five mongrel dogs were used. After mucoperiosteal flaps were raised, a midline strip of bone was removed from the hard palate of each dog to simulate the bony defect seen in a cleft palate. A transverse osteotomy was then made to separate the posterior segment of the hard palate from the anterior segment. Posterior osteotomies were also made laterally parallel to the teeth so that the two posterior segments (one on either side of the bony cleft) were mobile. An intraoral distractor that was partially submucosal was attached to the anterior hard palate and both segments of the mobilized posterior hard palate. Radio-opaque bone markers were placed, and X-rays obtained. After a 10 day latency period, the distractor was expanded 0.625 mm per day until 10.125 mm of distraction had been achieved. Distractors were left in place for an additional 2 to 3 months prior to sacrifice. Follow-up X-rays, tetracycline bone labeling, and histologic examinations were performed. New bone formation was found at the site of distraction in all dogs. This new bone was well seen on the follow-up X-rays, as well as on histologic examination of the hard palates using both H & E staining and tetracycline bone labeling.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A palate expander system comprising:

a first rigid section having a plane, having two or more members extending downwardly out of the plane, each member having a flat surface capable of being attached to a surface, and having one or more rigid guide members extending away from the first rigid section, a second rigid section having a plane, having two or more members extending downwardly out of the plane, each member having a flat surface capable of being attached to a surface, and having one or more receptacles to receive the one or more rigid guide members extending from the first rigid section, a threading system connecting the first and second rigid sections and capable of predictably adjusting the spacing between the first and second rigid sections, and screws for attaching the downwardly extending member flat surfaces to a patient's palate, wherein the first and second rigid sections can be incrementally adjusted to cause the palate to expand.

2. A method of lengthening a patient's palate which comprises the steps of:

(a) transversely separating a patient's palate into front and rear sections;

(b) providing an expander system of claim 1

(c) attaching the expander to a patient's palate by screwing the flat surfaces of the downwardly extending members of the first and second rigid section onto the front and rear sections of the patient's palate; and (d) incrementally elongating the distance between the first and second rigid sections to cause the distance between the palate sections to incrementally elongate, whereby the palate is lengthened.

3. A method of treating velopharyngeal incompetence, which comprises the steps of:

(a) transversely separating a patient's palate into front and rear portions;

(b) providing an expansion system of claim 1

(c) attaching the flat surfaces of the downwardly extending members of the first rigid section to one palate portion;

(d) attaching the flat surfaces of the downwardly extending members of the second rigid section to the other palate section;

(e) incrementally elongating the distance between the first and second rigid sections to cause the distance between the palate sections to incrementally elongate;

(f) allowing bone to fill in the space between the palate sections created in step (e); and (g) repeating steps (e) and (f) as many times as necessary to achieve a desired lengthening of the patient's palate.

* * * * *